US006878177B2

(12) United States Patent
Lohr et al.

(10) Patent No.: US 6,878,177 B2
(45) Date of Patent: Apr. 12, 2005

(54) INCUBATOR HAVING COMBINED HEPA AND VOC FILTER

(75) Inventors: David Lohr, Beverly, OH (US); Raquel Wager, Waverly, WV (US)

(73) Assignee: Thermo Forma, Inc., Marietta, OH (US)

( * ) Notice: Subject to any disclaimer, the term of this patent is extended or adjusted under 35 U.S.C. 154(b) by 193 days.

(21) Appl. No.: 09/941,186

(22) Filed: Aug. 28, 2001

(65) Prior Publication Data

US 2003/0041572 A1 Mar. 6, 2003

(51) Int. Cl.[7] .................................................. C12M 1/36
(52) U.S. Cl. .................. 55/385.2; 55/350.1; 55/417; 55/471; 55/486; 55/498; 219/407; 219/408; 219/520; 219/522; 600/22; 422/121; 422/122; 422/123; 422/124; 422/125
(58) Field of Search .............................. 55/350.1, 385.2, 55/417, 471, 486, 498, 470, 472; 219/407, 408, 520, 522; 600/22; 422/121–125, 99, 109; 436/183; 435/303.1

(56) References Cited

U.S. PATENT DOCUMENTS

| 3,002,895 A | 10/1961 | Freedman |
| 3,057,138 A | 10/1962 | Huxster |
| 3,505,989 A | 4/1970 | Truman |
| 3,576,721 A | 4/1971 | Mason |
| 3,659,063 A | 4/1972 | Peterson |
| 3,659,079 A | 4/1972 | Whittemore |
| 3,710,074 A | 1/1973 | Stewart |
| 3,729,603 A | 4/1973 | Foltz |
| 3,756,069 A | 9/1973 | Carswell |
| 3,797,172 A | 3/1974 | Cannon |
| 3,803,375 A | 4/1974 | Foltz |
| 3,833,451 A | 9/1974 | Wagner |
| 3,857,757 A | 12/1974 | Herrick |
| 3,887,436 A | 6/1975 | Haddad |
| 3,890,608 A | 6/1975 | Peterson |
| 3,929,584 A | 12/1975 | Mansfield |
| 3,936,284 A | 2/1976 | Mason |
| 3,948,732 A | 4/1976 | Haddad |
| 3,987,133 A | 10/1976 | Andra |
| 4,001,974 A | 1/1977 | Wright |
| 4,033,825 A | 7/1977 | Haddad |
| 4,039,775 A | 8/1977 | Andra |
| 4,109,676 A | 8/1978 | Price |
| 4,116,514 A | 9/1978 | Lawrence |

(Continued)

FOREIGN PATENT DOCUMENTS

| JP | 01013985 A | 7/1987 |
| JP | 01285185 A | 11/1989 |
| JP | 06245753 A | 9/1994 |
| WO | WO 98/51777 | 11/1998 |

OTHER PUBLICATIONS

Forma Scientific, Inc., *Reach In Conditioning Chamber*, Three Photographs of Unit Sold in 1980.

(Continued)

*Primary Examiner*—Minh-Chau T. Pham
(74) *Attorney, Agent, or Firm*—Wood, Herron & Evans, L.L.P.

(57) ABSTRACT

A controlled atmosphere incubator having an interior chamber adapted to be heated and humidified. An easily accessed blower is located within the gaseous environment of the incubator chamber and includes a HEPA filter and VOC filter readily replaceable by the user from within the chamber.

15 Claims, 4 Drawing Sheets

U.S. PATENT DOCUMENTS

| | | |
|---|---|---|
| 4,140,357 A | 2/1979 | Wolz et al. |
| 4,336,329 A | 6/1982 | Hesse et al. |
| 4,356,967 A | 11/1982 | Lunick |
| 4,398,091 A | 8/1983 | Passaro |
| 4,443,791 A | 4/1984 | Risgin et al. |
| 4,457,111 A | 7/1984 | Koike |
| 4,498,330 A | 2/1985 | Hosoya |
| 4,521,147 A | 6/1985 | King, Jr. et al. |
| 4,527,807 A | 7/1985 | Urbanick |
| 4,559,066 A | 12/1985 | Hunter et al. |
| 4,644,698 A | 2/1987 | Gerdes et al. |
| 4,668,854 A | 5/1987 | Swan |
| 4,689,303 A | 8/1987 | Kraft |
| 4,701,195 A | 10/1987 | Rosendall |
| 4,701,415 A | 10/1987 | Dutton |
| 4,716,536 A | 12/1987 | Blanchard |
| 4,730,479 A | 3/1988 | Pyke |
| 4,737,173 A | 4/1988 | Kudirka et al. |
| 4,786,298 A | 11/1988 | Billiet et al. |
| 4,786,784 A | 11/1988 | Nikodem |
| 4,789,283 A | 12/1988 | Crawford |
| 4,841,283 A | 6/1989 | Bulbiewicz |
| 4,896,143 A | 1/1990 | Dolnick |
| 4,935,371 A | 6/1990 | Rickloff |
| 4,952,783 A | 8/1990 | Aufderheide et al. |
| 5,005,523 A | 4/1991 | Foster |
| 5,021,074 A | 6/1991 | Kovacik |
| 5,028,759 A | 7/1991 | Finley |
| 5,047,348 A | 9/1991 | Stinson |
| 5,066,111 A | 11/1991 | Singleton |
| 5,090,617 A | 2/1992 | Swan |
| 5,119,467 A | 6/1992 | Barsky et al. |
| 5,125,889 A * | 6/1992 | Snyders ............... 600/22 |
| 5,145,494 A | 9/1992 | Sowinski |
| 5,161,329 A | 11/1992 | Brown |
| 5,193,709 A | 3/1993 | Brassell |
| 5,217,692 A | 6/1993 | Rump |
| H1240 H | 10/1993 | Tardiff, Jr. et al. |
| 5,252,206 A | 10/1993 | Gonzalez |
| 5,342,676 A | 8/1994 | Zagdoun |
| 5,348,563 A | 9/1994 | Davis |
| 5,352,414 A | 10/1994 | Rothenberg |
| 5,354,966 A | 10/1994 | Sperbeck |
| 5,360,469 A | 11/1994 | Baron et al. |
| 5,416,931 A | 5/1995 | Wolfenden |
| 5,418,131 A | 5/1995 | Butts |
| 5,424,209 A | 6/1995 | Kearney |
| 5,493,994 A | 2/1996 | Cox et al. |
| 5,514,196 A | 5/1996 | Tanahashi et al. |
| 5,569,005 A | 10/1996 | Millington |
| 5,598,807 A | 2/1997 | Cox et al. |
| 5,626,820 A | 5/1997 | Kinkead et al. |
| 5,772,738 A | 6/1998 | Muraoka |
| 5,792,427 A | 8/1998 | Hugh et al. |
| 5,827,339 A | 10/1998 | Nagafune et al. |
| 5,833,726 A | 11/1998 | Kinkead et al. |
| 5,834,069 A * | 11/1998 | Berman et al. ............. 427/553 |
| 5,882,918 A | 3/1999 | Goffe |
| 5,893,939 A | 4/1999 | Rakocy et al. |
| 5,922,105 A | 7/1999 | Fujii et al. |
| 5,933,702 A | 8/1999 | Goswami |
| 5,942,974 A | 8/1999 | Pfreundschuh et al. |
| 5,964,182 A | 10/1999 | Cox et al. |
| 5,967,080 A | 10/1999 | Cox et al. |
| 5,983,830 A | 11/1999 | Cox et al. |
| 6,013,119 A | 1/2000 | Cecchi et al. |
| 6,117,687 A | 9/2000 | Hugh |
| 6,143,048 A * | 11/2000 | Comproni et al. ............ 55/356 |
| 6,146,266 A * | 11/2000 | O'Halloran et al. ........ 454/187 |
| 6,200,362 B1 | 3/2001 | Cecchi et al. |
| 6,225,110 B1 | 5/2001 | Cecchi et al. |
| 6,402,681 B1 * | 6/2002 | McDonough et al. ......... 600/22 |
| 6,508,989 B1 * | 1/2003 | Urrusti et al. ............. 422/121 |

OTHER PUBLICATIONS

GenX International, *Coda Incubator Unit*, Brochure, Oct. 1999, pgs.

Forma Scientific, Inc., *Forma Direct Heat CO2 Incubators*, Brochure, 9/00, 8 pgs.

Revco Scientific, *Revco Ultima Laboratory CO2 Incubators*, 1992, 6 pages.

Forma Scientific, Inc., *Understanding Automatic CO2 Control Systems*, 1981, 8 pages.

Forma Scientific, Inc., *Reach In Conditioning Chamber*, Photograph of Unit Sold in 1982.

Nova In Vitro Foundation, *Air Quality in Tissue Culture Laboratories and Air Purifying Devices*, 1997 Letter and Sales Information of In Vitro Foundation, 6 pgs.

Revco Scientific, *Revco Laboratory CO2 Incubators*, Brochure, 1995, 14 pages.

Revco Scientific, *Revco Ultima Laboratory CO2 Incubators*, 1993, unpaginated, 6 pgs.

Revco Scientific, *Revco Laboratory CO2 Incubators*, 1995, unpaginated, 8 pgs.

Forma Scientific, Inc., *Forma Series II Universal Water Jacketed Incubators*, Brochure, 7/O0, 12 pgs.

Jacques Cohen et al., *Ambient Air and Its Potential Effects on Conception*, 1992 Article, 8 pgs.

* cited by examiner

INCUBATOR HAVING COMBINED HEPA AND VOC FILTER

FIELD OF THE INVENTION

The present invention is generally related to controlled atmosphere incubators and, more specifically, to an improved incubator used to culture biological specimens.

BACKGROUND OF THE INVENTION

Incubators are used in laboratories to maintain as viable bacteria, cells, tissues, and other biological specimens. Incubators accomplish this by providing a controlled environment. There are many parameters of the incubator environment which require control. These include temperature, humidity, and the concentration of gases such as oxygen and carbon dioxide, among others. An air circulation system is a vital ingredient in creating the correct environmental conditions for the growth of cell cultures in a laboratory incubator. Air circulation is needed to maintain temperature uniformity within the chamber and also to effectively distribute and mix the various gases, such as $CO_2$ and $N_2$, used to control the pH and $O_2$ levels within the chamber. The air flow keeps the lighter gases from stratifying within the chamber and aids in the control of $CO_2$ and $O_2$ levels by providing air flow across the gas sensors. A blower is generally used in conjunction with a high efficiency particulate air or "HEPA" filter for circulating the air and removing contaminants from the air. The HEPA filters must be maintained at a temperature above the dew point of the air mixture to prevent condensation from developing inside the filter. This condensation can restrict or block the flow of air through the filter. Problems which existed with such air circulation systems included the requirement for an additional heat source to maintain the temperature of the HEPA filter above the dew point of the air mixture. Also, HEPA filters have generally been mounted in locations requiring the removal of side panels and other hardware associated with the incubator in order to access the filter for replacement. As the researcher or operator may be exposed to high voltage components when removing these incubator panels, a qualified service technician must be used for what should otherwise be a simple filter replacement procedure.

These problems were addressed in U.S. Pat. No. 5,792,427 by providing a HEPA filter located within the gaseous environment of the interior chamber of the incubator. As previously mentioned, the air flow pattern within the incubator is created by a high volume air blower mounted within the incubator chamber in an easily accessible manner. Air is pulled into a blower near the top of the chamber and exhausted through duct work that runs across the top of the chamber, down a plenum located behind a side wall of the chamber and across the bottom of the chamber until the air disperses and is pulled up vertically through perforated shelves located inside the chamber. In the preferred embodiment of U.S. Pat. No. 5,792,427, a HEPA filter is mounted directly to the blower and is located internally to the chamber. Therefore, the HEPA filter does not require an additional heat source to maintain its temperature above the dew point of the air mixture within the chamber. The HEPA filter is also easily removed and replaced by a researcher or other user from within the chamber and does not require the removal of side panels or other hardware which might involve exposure to high voltage wiring and/or components.

Thus, filtering the gaseous environment of an incubator to remove particulate materials, as with a HEPA filter, is known in the art. However, particulate materials are not the only potential source of contamination in an incubator. For example, volatile organic compounds (VOCs) may also be present within the incubator chamber. VOCs are not removed by a HEPA filter, and as such, could have a harmful effect on the samples within the incubator chamber.

There are many sources of VOCs. They may be present in the atmosphere of the room in which the incubator is located often in greater concentrations than air outside a laboratory. Sources of VOC contamination in the laboratory include general air contamination, cleaning agents, and off-gassing laboratory equipment and plasticware. VOCs include organics, such as alcohols, aldehydes, ketones, esters, aliphatics, aromatics and chlorinated hydrocarbons. When the incubator is opened, these VOCs may enter the incubator chamber. In addition to this means of contamination, the supply of gases such as carbon dioxide and oxygen to the incubator environment from an external supply may provide a direct path of ingress for the undesirable VOCs. Compounds and solutions used in culturing techniques may also contribute to contamination by unwanted VOCs.

It would thus be desirable to filter VOCs from the incubator in order to improve the quality of and to better control the atmosphere of the incubator. As an example of this, a system and method for filtering VOCs from incubators is disclosed in U.S. Pat. No. 6,013,119. According to the disclosure of that patent, there is provided a stand-alone filter system for an incubator for filtering VOCs and particulate material from the gaseous environment within the incubator. This system uses an inlet for receiving a gas stream from the gaseous environment of the incubator; an outlet for returning the gas stream to the gaseous environment of the incubator; and a filter connected between the inlet and outlet for filtering the stream of gas in order to filter VOCs and particulate material from the gas stream. In each embodiment of the incubator of U.S. Pat. No. 6,013,119, air is removed from the gaseous environment of the incubator cabinet at a low flow rate into a stand-alone filter unit and then returned to the gaseous environment of the incubator through the action of a low flow rate pump.

While U.S. Pat. No. 6,013,119 is one example of a VOC filter being used in conjunction with an incubator, a number of drawbacks still exist with the apparatus and method disclosed in that patent. For example, these current incubators incorporating stand-alone VOC filters use a low flow rate pump which circulates air at a rate equal to or less than about 0.3 liters per minute. The purpose of this low flow rate is to ensure that the air stream has enough residence time in the filter to maximize the filtering of contaminates. However, an increase in the time it takes a VOC filter to decontaminate one cycle of air correlates to an increased amount of time that any VOC may remain viable in the incubator prior to passing through the filter. These problems are compounded by, and some additional problems arise from, the location of the VOC filter in conjunction with currently existing incubators. As previously mentioned, these stand-alone units are segregated from the gaseous environment on the incubator chamber. Some are even located outside the incubator itself. This increases the distance the air stream must travel and thus the time necessary for filtering one cycle of air. Also, the location of the VOC filter may make it difficult to reach for repair, replacement, and/or cleaning. This results in problems of increased expense and time to perform these maintenance functions. All these problems may ultimately result in an increased degree of VOC contamination of the contents of the incubator.

In view of the above noted problems and deficiencies of incubators in general, there is a need for an incubator which provides a more accurate simulated chamber condition and which is more easily operated and maintained in the field by the end user. Further, it would be desirable to provide an incubator incorporating both a VOC and a HEPA filter which can maintain a high airflow and filtering rate and allows for easy maintenance.

SUMMARY OF THE INVENTION

The controlled atmosphere incubator of the present invention solves the problems and eliminates the drawbacks described in the background of the invention. It does so by providing a controlled atmosphere incubator including a cabinet in thermal communication with a heater for maintaining a required temperature. The cabinet includes top, bottom, rear, and side walls defining an interior chamber of the incubator. Access to this interior chamber is provided by a door pivotally mounted to the front of the incubator. A blower is mounted within the chamber and includes both an inlet and an outlet for aiding in air circulation within the chamber. The chamber also includes an upper plenum partially formed by a plate mounted across the chamber and between the inlet and outlet of the blower. The circulation of air in the incubator proceeds through this upper plenum which then adjoins a side plenum that conveys the air to an opening in the base of the process chamber. A VOC filter is operatively connected to the inlet of the blower to filter VOCs from the atmosphere of the incubator. This need not be a physical connection, but one which facilitates the filtering function. This VOC filter surrounds a HEPA filter which removes particulate matter from the atmosphere of the chamber. The VOC and HEPA filters are integrated into the air flow system of the incubator chamber itself and are contained within the gaseous environment of the incubator chamber.

The blower typically includes an AC motor, a scroll, and a blower wheel designed to move air through the incubator at a rate of at least 5 cubic feet/minute (cfm). In one embodiment, the blower will move the air through the incubator at a rate of 6–7 cfm. The blower draws gas through a filter located at the top of the process chamber. Filtered gas is discharged from the outlet of the blower and flows through an upper plenum. The upper plenum adjoins a side plenum that conveys the filtered gas to an opening in the base of the process chamber. The filtered gas is exhausted from the opening over a water-filled pan to humidify the filtered gas as it re-enters the process chamber.

The VOC and HEPA filter elements are contained directly within the gaseous environment of the incubator chamber. One benefit of this improvement is that VOC contamination is eliminated from the gas mixture as it is quickly and completely circulated through the incubator. Since the combined filter is integrated as part of the standard blower system of the incubator, and since the air moves at 6–7 cfm through the filter, the entire mass of air in the processing chamber is filtered approximately once a minute in a chamber having a volume of 6.5 cfm. This filtering occurs much more rapidly than in incubators of the prior art while eliminating both VOCs and particulate materials. As a result, the purity of the gas mixture within the process chamber will be enhanced over other filter systems.

Additionally, the location of the VOC and HEPA filters in the interior of the incubator chamber tremendously simplifies any repair or replacement procedures over those necessary with incubators of the prior art. The filters are easily removed and replaced by a researcher or other user from within the chamber and do not require the removal of side panels or other hardware which might involve exposure to high voltage wiring and/or components.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

DETAILED DESCRIPTION OF THE INVENTION

Figure 1:
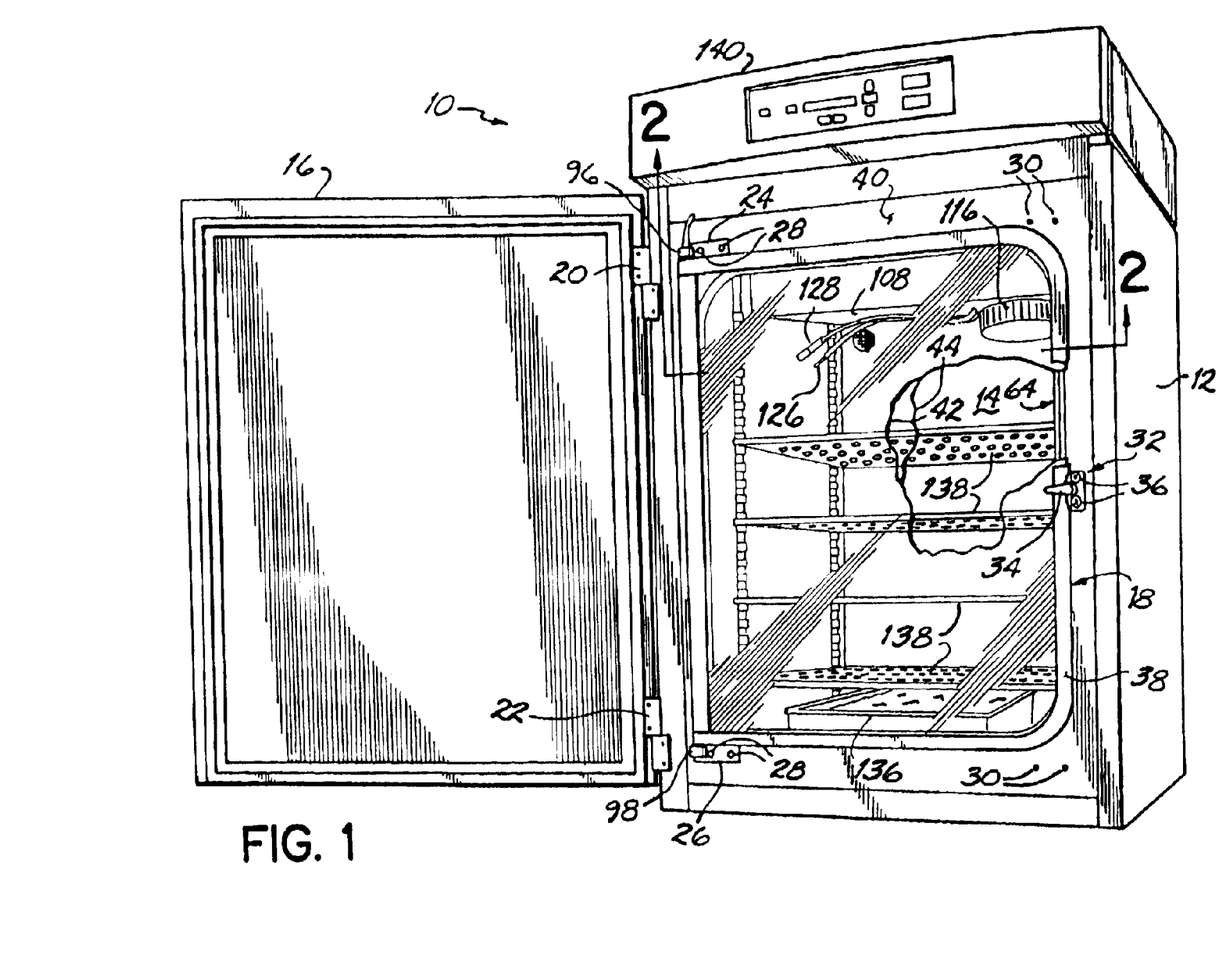
FIG. 1 is a perspective view of an incubator constructed in accordance with the present invention.

FIG. 1 illustrates an incubator 10 constructed in accordance with the present invention and generally including an insulated, and preferably water-jacketed, cabinet 12 with an interior controlled-atmosphere chamber 14. Chamber 14 is accessed through a pair of doors which include an outer insulated door 16 and an inner heated glass door 18. Insulated door 16 is attached to cabinet 12 by a pair of hinges 20, 22 which may be alternatively attached to the left or right side of cabinet 12 depending on which direction it is desired to swing insulated door 16. Likewise, inner glass door 18 includes hinges 24, 26 secured by fasteners 28 to front panel 40 of cabinet 12. In general these fasteners 28 and receiving elements 30 allow fastening of door 18 to front panel 40 in either a left or right swinging manner. Fastener receiving elements 30 are installed permanently on both the left and the right side of front panel 40 and are sealed into the water jacket portion of cabinet 12. Door 18 further includes a latch assembly 32 having a twist latch 34 fastened to front panel 40 by fasteners 36. Latch 34 bears against frame 38 of door 18 when in the latched position to seal door 18 against front panel 40 as will be described below.

Figure 2:
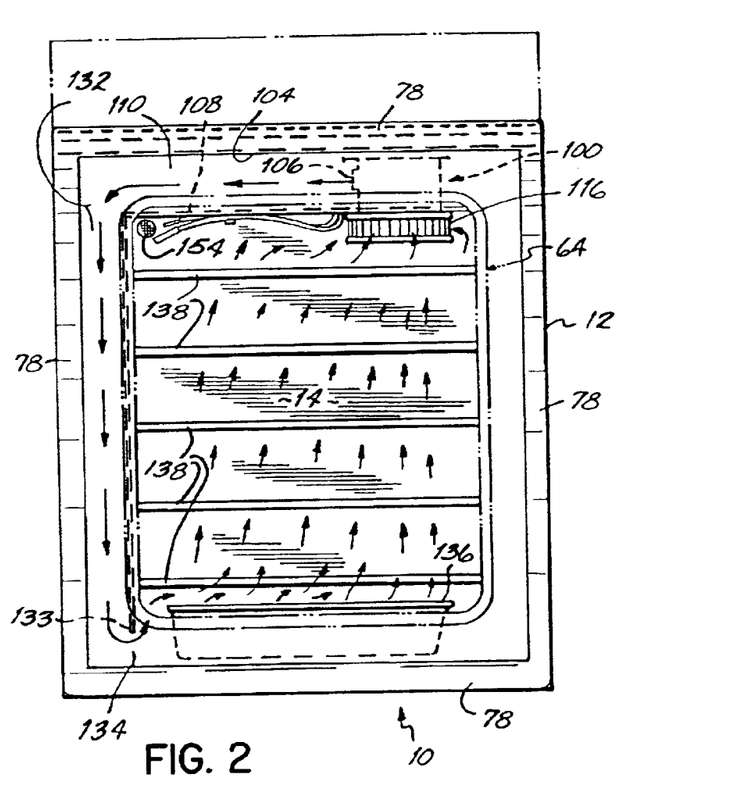
FIG. 2 is a diagrammatic front view showing the air flow pattern and blower within the incubator chamber.
Figure 3:
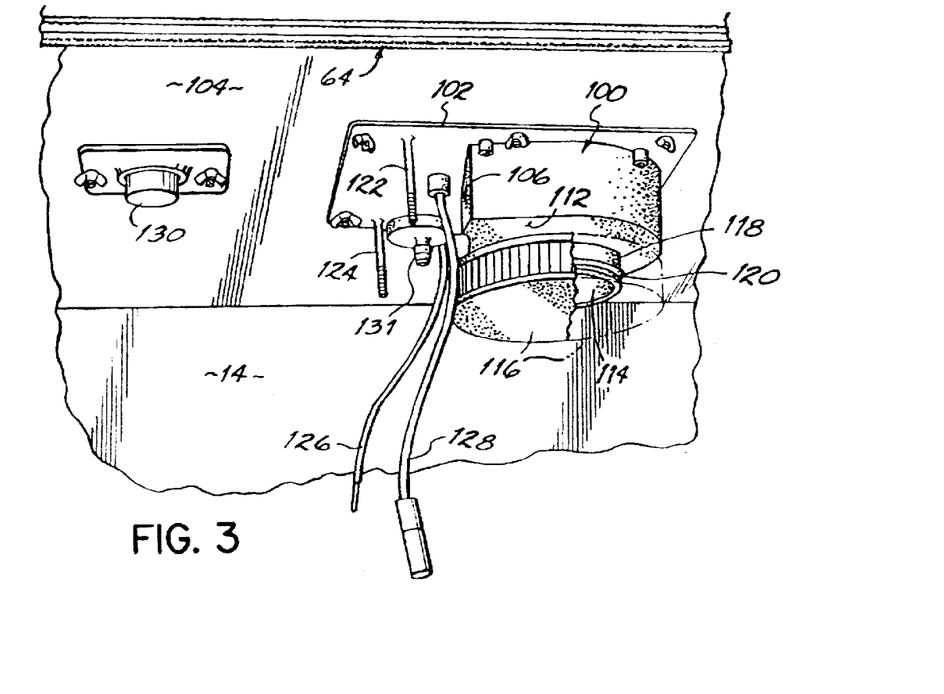
FIG. 3 is a fragmented perspective view showing the blower and a $CO_2$ sensor at the top of the incubator chamber with an upper plenum-defining plate removed for clarity.
Figure 4:
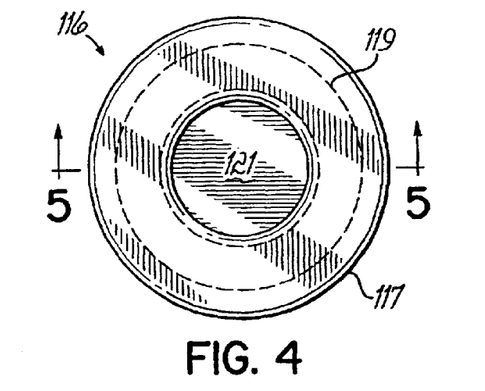
FIG. 4 is a top view of the VOC/HEPA filter assembly in accordance with the present invention.

Referring now to FIGS. 2 and 3, the air circulation system of the invention includes a blower 100 which is mounted to a plate 102 (FIG. 3) at an upper end of chamber 14. Blower 100 is a high flow rate blower that moves air at a rate of at least 5 cfm. Mounting plate 102 is fastened to an upper panel 104 of chamber 14. As appreciated from FIG. 2, an outlet 106 of blower 100 is situated between panel 104 and a panel 108. An upper plenum 110 is defined between panels 104, 108 and extends across the top of chamber 14. In FIG. 3, panel 108 has been removed for clarity but, in practice, sits against surface 112 of blower 100 between outlet 106 and an inlet 114 to which is attached a VOC/HEPA filter assembly 116 including both a VOC filter 117 and a HEPA filter 119 (seen in FIG. 4B). Filter assembly 116 is mounted to a cylindrical extension 118 defining inlet 114 of blower 100. Extension 118 includes a circular O-ring seal 120 for sealing the removable connection made between filter assembly 116 and extension 118. As appreciated from FIG. 2, filter assembly 116 may be easily removed and replaced from within chamber 14. Plate 108 is removably fastened in the upper portion of chamber 14 to a pair of threaded elements 122, 124 extending downwardly from mounting plate 102. Thus, plate 108 may also be easily removed to allow maintenance and replacement of the entire blower 100 from within chamber 14. Also extending from plate 102 is a temperature probe 126 and a humidity sensor 128. Probe 126 and humidity sensor 128 are connected to further control hardware located at the top of incubator 10. Also contained within upper plenum 110 is a $CO_2$ sensor 130 which may be of a thermal conductivity or infrared variety. The $CO_2$ sensor 130 is therefore mounted in the path of filtered air exiting blower 100 and may also be easily accessed from within chamber 14 after removing plate 108. A VOC and HEPA filtered sample port 131 is also mounted to plate 102 for drawing test samples of air from chamber 14.

Figure 5A:
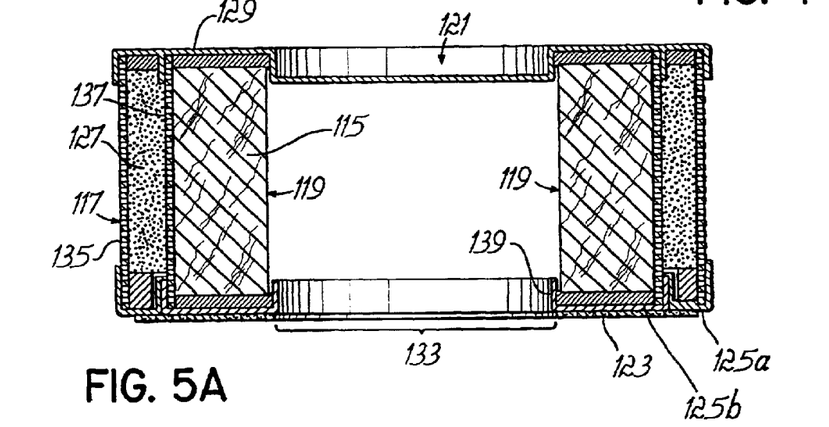
FIG. 5A is a cross-sectional view of the VOC/HEPA filter assembly in accordance with the present invention taken along lines 5—5 of FIG. 4.

Referring now to FIGS. 4 and 5A, a more detailed view of the VOC/H EPA filter assembly 116 is depicted Filter assembly 116 is substantially cylindrical. As can be seen in the illustrated embodiment, the cross-section of filter assembly 116 taken along a plane perpendicular to the axis of symmetry of the filter assembly 116 is circular. Also in the illustrated embodiment, the cross-section of the filter assembly 116 taken along a plane parallel to the axis of symmetry of the filter assembly 116 is substantially rectangular (as depicted in FIG. 5A). Filter assembly 116 includes an end cap 129 having a central cylindrical depression 121, a flanged end cap 125a on the VOC filter 117, and a flanged end cap 125b on the HEPA filter 119. The cylindrical depression 121 is diametrically larger than the cylindrical extension 118 (FIG. 3) such that cylindrical extension 118 can be positioned within an opening 133 of similar diameter which is located opposite the cylindrical depression 121 and peripherally within the inner diameter of the annular HEPA filter 119. Thus, depression 121 facilitates the mounting of filter assembly 116 to cylindrical extension 118 by defining the diameter of opening 133. As previously described, O-ring seal 120 is used to seal the removable connection between filter assembly 116 and extension 118. A circular sealing surface 139 is provided on the inner periphery of end cap 125b. When the VOC/HEPA filter assembly 116 is mounted to the extension 118, sealing surface 139 frictionally engages the O-ring seal 120.

As can be seen with reference to FIG. 5A, the VOC filter 117 surrounds the outer circumference of the HEPA filter 119 in the VOC/H EPA filter assembly 116 of the incubator 10 of the present invention. Thus, the filter assembly 116 combines two separate forms of media in two separate "layers" to filter both volatile organic compounds and airborne particulates. The inner "layer" of the filter assembly 116 is a HEPA filter 119 including a HEPA filter material 115. As used herein, the term "HEPA" will be used to refer to either or both of HEPA-rated filters and ULPA-rated filters. In one embodiment, the HEPA filter material 115 is selected such that the HEPA filter 119 is 99.97% efficient at removing particulate material having a diameter as small as 0.3 microns from the gaseous environment of the incubator chamber 14. In one particular embodiment, the HEPA filter material 115 includes pleated fiberglass spaced with adhesive beads. In other embodiments, the HEPA filter material 115 is selected such that the HEPA filter 119 is 99.999% efficient at removing particulate matter having a diameter as small as 0.12 microns.

The outer "layer" of the HEPA/VOC filter assembly 116 is a VOC filter 117 including at least one molecular sieve adsorbent 127 that can remove VOCs from the gaseous environment of the incubator chamber 14. In alternate embodiments, the VOC filter 117 may include two or more different molecular sieve adsorbents. Each adsorbent 127 has a different pore structure for adsorbing a variety of molecules of different sizes. The VOC filter 117 may include any adsorbent material known to those skilled in the art that is useful in filtering VOCs from the gaseous environment within the incubator chamber. Among other adsorbent materials, materials such as carbon and silica may be used, as will be described in more detail below.

The VOC filter 117, disposed circumferentially about the outer diameter of the HEPA filter 119, forms a sidewall around the HEPA filter 119. Thus, the airflow within the incubator chamber passes directly through VOC filter 117, and ultimately into upper plenum 110. However, the airflow enters the HEPA filter 119 by a stream of airflow that first passes through the VOC filter 117 and subsequently into the HEPA filter 119. Airflow is drawn through filter assembly 116 by the operation of the blower 100. Blower 100 includes a blower motor, blower wheel, and blower scroll (not shown). The HEPA filter 119 is operatively connected to extension 118 which includes an inlet 114 on the blower scroll.

In the illustrated embodiment of the incubator of the present invention (depicted in FIGS. 4 and 5A), the VOC filter 117 and HEPA filter 119 may be adjoined and sealed one to another by an adhesive ring seal 123 disposed across and between the end cap 125a of the VOC filter 117 and the end cap 125b of the HEPA filter 119. In the illustrated embodiment of the present invention, the adhesive ring seal 123 includes Mylar tape. This adhesive ring seal 123 is shaped as an annulus and is adhered to both the bottom side of the HEPA filter 119 and the bottom side of the VOC filter 117 so as to span the confronting side edges of the VOC and HEPA filters 117, 119. In alternative embodiments of the present invention, any sealant material having properties to adjoin and seal the VOC filter 117 with the HEPA filter 119 may be used, such as glues or cement. Additionally, in alternate embodiments of the present invention the sealant may be applied to either the top sides or bottom sides or both sides of the VOC and HEPA filters 117, 119. The VOC and HEPA filters 117, 119 are attached to the end caps 125a, 125b, 129, for example, with a conventional adhesive, such as a urethane adhesive.

As described above, the VOC filter 117 may include any adsorbent material 127 known to those skilled in the art that is useful in filtering VOCs, and particularly, those useful in filtering VOCs from a gaseous environment within an incubator chamber. Suitable materials include carbon, activated carbon, activated charcoal, silica, zeolites, and combinations thereof, although other materials capable of filtering VOCs may be used. Positioned adjacent the radial faces of the VOC filter 117 are a perforated outer liner 135 and a perforated inner liner 137, which may each be formed of a polymer, that are configured to permit radial airflow through the VOC filter 117 while confining or otherwise capturing the adsorbent material 127, which may comprise a particulate or a powder or may include a component that is granular.

In one embodiment of the present invention, the adsorbent material used in the VOC filter 117 is a high-silica zeolite adsorbent, referred to herein as a HiSiv adsorbent. High-silica zeolite adsorbents suitable for use with the present invention are marketed, for example, under the trade name HiSiv by UOP Molecular Sieves (Des Plaines, Ill.). HiSiv adsorbents are developed from high-silica molecular sieves and are hydrophobic and selective for organic molecules in the presence of water. Chemically, most HiSiv adsorbents suitable for use in the VOC filter 117 are crystalline, inorganic silica-alumina structures. However, other structures for the HiSiv adsorbent is contemplated by the present invention. HiSiv adsorbents exhibit a high capacity for retaining VOCs at low concentrations. This characteristic permits easy VOC removal to less than 1 ppm in the gaseous environment of the incubator chamber. HiSiv adsorbents are non-combustible and non-reactive to most compounds and adsorb organics such as alcohols, aldehydes, ketones, esters, aliphatics, aromatics and chlorinated hydrocarbons.

More specifically, the HiSiv adsorbent of the first embodiment is a molecular sieve adsorbent that includes a pore structure for adsorbing VOC molecules. The pores provided by the HiSiv adsorbent have diameters up to about 0.8 nm. The HiSiv adsorbent is provided as $1/16$ inch to $1/8$ inch pellets in those applications where pressure drop constraints are limiting, or alternatively, is provided in a powder from for incorporation into monolithic forms. Pelletized HiSiv adsorbent for use with the present invention is marketed under the trade name HISiv by UOP Molecular Sieves (Des Plaines, Ill.). HiSiv adsorbents are particularly useful in adsorbing larger molecules (those having diameters in the range of about 0.6 nm to about 0.8 nm) and higher boiling solvents such as toluene and methyl isobutyl ketone. The VOC filter 117 using HiSiv adsorbents is up to 99.9% efficient at removing VOCs from the gaseous environment of the incubator chamber. HiSiv adsorbents can be regenerated for re-use by elevated temperature and/or reduced pressure purging with air, steam or other gases. The thoroughness of regeneration is dependent on the temperature, pressure and quantity of the purge gas.

In another embodiment of the present invention, the adsorbent material 127 present in the VOC filter is activated carbon. In other alternative embodiments, mixtures of adsorbents, such as activated carbon and HiSiv adsorbent, may be included in the VOC filter 117 of the incubator 10 of the present invention.

The VOC filter 117, may also include media to be used as a substrate or binder for the adsorber. The media can include any known, non-electrically conducting, inorganic material. Porous materials suitable for use as a substrate media include ceramic-based materials, glass-based materials, and combinations thereof. Materials that are particularly suitable include, but are not limited to, cordierite, mullite, clay, talc, zircon, zirconia, alumina, silica, silicates, borides, nitrides, carbides, or mixtures thereof. The substrate utilized may also be in a variety of forms, including honeycombs, or multi-cellular bodies having a spacing which would allow for efficient passage of airflow from the gaseous environment of the incubator 10 through the VOC filter 117, for example, in those instances in which a reduced pressure drop in the airflow across the VOC filter 117 is desired.

Figure 5B:
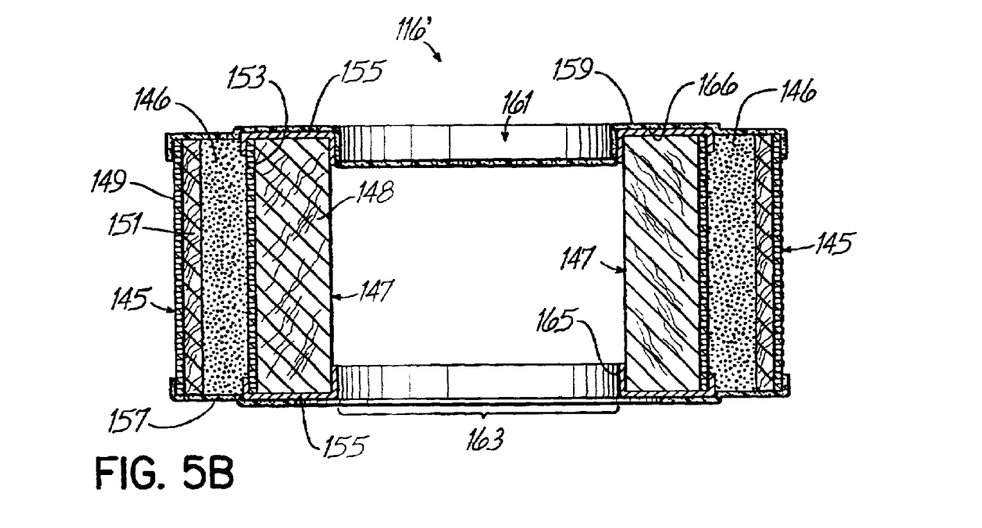
FIG. 5B is a cross-sectional view, similar to FIG. 5A, of another embodiment of a VOC/HEPA filter assembly in accordance with the present invention.

Referring to FIG. 5B, another embodiment of a VOC/HEPA filter assembly 116' of the present invention includes an annular VOC filter 145 having a cylindrical outer periphery and an axially-extending cylindrical inner bore and an annular HEPA filter 147 positioned within the cylindrical inner bore of the VOC filter 145. As described above with regard to VOC filter 117 (FIGS. 4 and 5A), the VOC filter 145 operates to remove volatile organic compounds from the radially-inward airflow from the gaseous environment inside the chamber 14 (FIG. 1) into and through the filter assembly 116'. To that end, the VOC filter 147 includes any adsorbent material 146 known to those skilled in the art that is useful in filtering volatile organic compounds from the gaseous environment within the incubator chamber 14. As described above with regard to adsorbent material 127 for use in VOC filter 117, materials suitable for use as adsorbent material 146 include, but are not limited to, a molecular sieve adsorbent, an activated carbon, and a HiSiv adsorbent, which may be provided in combinations of materials and/or which may be attached to, or incorporated into, a substrate.

The HEPA filter 147 includes a HEPA filter media or material 148, which may be pleated or corrugated, operable to remove airborne particulates from the radially-inward airflow into and through the filter assembly 116'. In certain embodiments, the HEPA filter material 148 may be any air-permeable, HEPA-rated filter media that provides for capture of 99.97% or greater of particulates having a diameter as small as 0.3 microns from the radially-inward airflow, with collection of particulates on the internal surfaces of the filter media. In one particular embodiment, the HEPA filter material 148 may be a HEPA-rated glass micro-fiber media, such as a LydAir® HEPA air filtration media available commercially from Lydall, Inc. (Manchester, Conn.) or, more specifically, a LydAir® Grade 3428, Class 3000 HEPA air filtration media. HEPA filter material 115 (FIG. 5A) may take a similar form. In other embodiments, the HEPA filter material may be any air permeable ULPA-rated filter media, such as those made of glass fibers, that provides for capture of 99.999% or greater of particulates having a diameter as small as 0.12 microns.

The VOC filter 145 forms a substantially-sealed, circumferential sidewall around the HEPA filter 147 so that the radial airflow, drawn into the VOC/HEPA filter assembly 116 by the operation of the blower 100, serially passes through the VOC filter 145 and the HEPA filter 147 before entering the upper plenum 110 for subsequent return circulation of a filtered airflow back into chamber 14. The VOC filter 145 includes an annular perforated layer 149 and an annular porous layer that are disposed peripherally about an outer circumference of the adsorbent material 146. The perforated layer 149 is positioned radially outward from the porous layer 151, which is provided to prevent outward loss or escape of particles, such as small particles or fines, originating from the adsorbent material 146. The porous layer 151 preferably presents a minimal pressure drop for the airflow through the filter assembly 116'. The perforated layer 149 may take the form of a perforated polymer screen such as a polypropylene screen having pinhole-like perforations. The annular porous layer 151 may be formed of, for example, a spun-bonded polyester fabric such as a Reemay® spun-bonded polyester fabric or, more specifically, a Reemay® Style 2040 spun-bonded polyester fabric, which are available commercially from companies such as Reemay, Inc. (Old Hickory, Tenn.).

The HEPA filter 147 further includes an annular perforated layer 153, such as a perforated polymer screen or, more specifically, a perforated polypropylene screen, that is disposed radially between an inner circumference of the VOC filter 145 and an outer circumference of the HEPA filter 147. The perforated layer 153 separates the adsorbent material 146 from the HEPA filter material 148 and inhibits the inward migration of the adsorbent material 146. A pair of annular, flanged end caps 155 are positioned in a confronting relationship for holding the perforated layer 153 proximate the outer circumference of the HEPA filter material 148 and to capture the HEPA filter material 148 therebetween. The HEPA filter material 148 and the perforated layer 153 are attached to the end caps 155 with, for example, an adhesive such as a urethane adhesive.

The VOC filter 145 and the HEPA filter 147 are positioned between a flanged annular housing 157 and a flanged disk-shaped housing 159. The VOC filter 145 and the HEPA filter 147 are attached to the housings 157, 159 with, for example, an adhesive such as a hot melt thermoplastic adhesive. Provided in the disk-shaped housing 159 is a stepped annular recess 166 that assists in locating the VOC filter 145 and the HEPA filter 147 relative to housing 159. The disk-shaped housing 159 also includes a central cylindrical depression 161, similar to cylindrical depression 121 (FIGS. 4 and 5A), that is diametrically larger than the cylindrical extension 118 (FIG. 3) such that cylindrical extension 118 can be positioned within an opening 163 of similar diameter. The diameter of the opening 163 is substantially equal to the diameter of an inner circumference of the HEPA filter 147. As previously described, the O-ring seal 120 (FIG. 3) seals the removable connection between filter assembly 116 and cylindrical extension 118. Specifically, a circular sealing surface 165 is provided on the inner periphery of the end cap 155 adjacent to opening 163. Sealing surface 165 engages the outer circumference of the O-ring seal 120 in a frictional engagement when the VOC/HEPA filter assembly 116' is mounted to extension 118.

With reference to FIG. 2, chamber 14 further includes a side plenum 132 which connects with upper plenum 110 and which has a lower opening 134. Air is drawn into the VOC and HEPA filtered inlet 114 (FIG. 3) of blower 100, exits across upper plenum 110 and past $CO_2$ sensor 130. The filtered air then moves downwardly through side plenum 132, through opening 134 and across a conventional pan 136 which holds water for humidifying chamber 14. As shown in FIG. 1, shelves 138 mounted within chamber 14 are perforated to allow air circulation upwardly and finally back through filter assembly 116.

Figure 6:
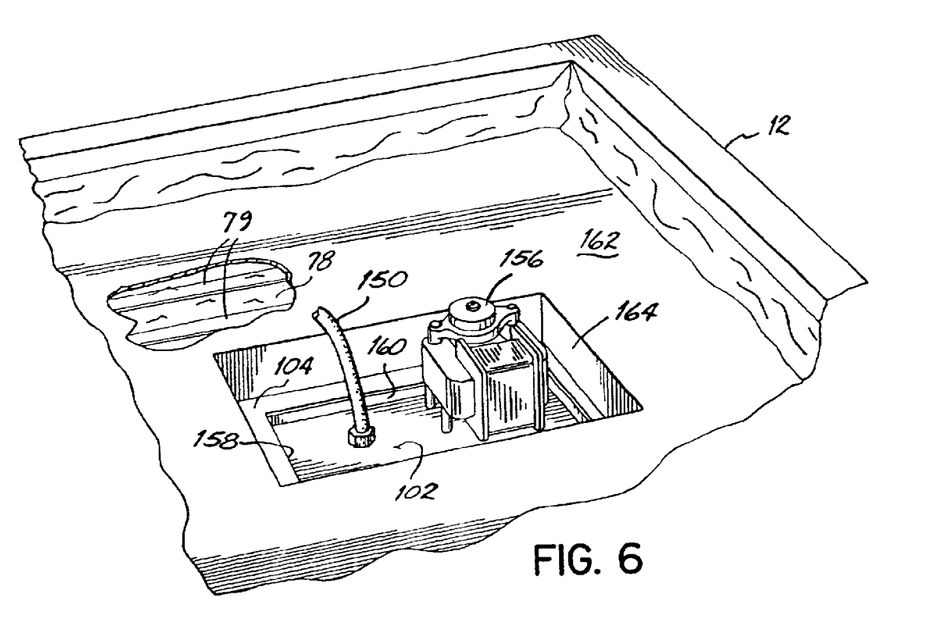
FIG. 6 is a perspective view of the interior top of the incubator cabinet which holds the motor for operating the blower.

Referring now to FIG. 6, a motor 156 is secured to mounting plate 102 and extends through an opening 158 in upper panel 104. A gasket 160 is disposed between mounting plate 102 and upper panel 104. This arrangement allows motor 156 to be mounted outside of chamber 14 but directly adjacent thereto so that it may be easily connected to blower 100 (see FIGS. 2 and 3). A top section 162 of water jacket 78 is formed with a portion 164 cut out to allow the mounting of motor 156 directly against mounting plate 102 and to also allow the filtered ambient air inlet 150 as well as other control components to extend into chamber 14. As also shown in FIG. 6, water jacket 78 preferably includes electric heating elements 79 for directly heating the water therein and indirectly heating chamber 14 in a uniform manner. It will be understood that the present invention may be utilized in other types of incubators such as, for example, direct heat models and sterilizing models.

In use, the motor 156 of blower 100 is used to draw the air of the gaseous environment of the interior of the incubator chamber 14 into the inlet 114 of blower 100. As air flows into blower 100, it is passed through the VOC/filter assembly 116 located within the gaseous environment of the incubator 10. First, air passes through VOC filter 117, which operates to remove VOCs such as acetone, chlorine, glycol, and toluene, among others, from the air. Subsequently, air is passed through the HEPA filter 119, which removes particulate material. Air is then discharged from the blower 100 through an outlet 106 and into the upper plenum 110 of the chamber 14. Air flows from upper plenum 110 to side plenum 132 and re-enters incubation chamber 14 at the bottom of the chamber 14. Air is moved through the incubator chamber 14 at a rate of about 6–7 cfm. This filtering occurs more rapidly than in incubators of the prior art while eliminating both VOCs and particulate materials.

From the above disclosure of the general principles of the present invention and the preceding detailed description of various embodiments, those skilled in the art will readily comprehend the various modifications to which this invention is susceptible. Therefore, the invention should not be considered limited to such embodiments, but may be used in other ways without departure from the essential features thereof.

What is claimed is:

1. A controlled atmosphere incubator comprising:
   a heater;
   a cabinet including a chamber housing a gaseous environment, said chamber being in thermal communication with the heater and surrounded by top, bottom, rear and side walls and having a front side with an opening;
   an outer door pivotally mounted to said front side;
   a high flow rate blower mounted within said cabinet and including an inlet and an outlet, wherein said high flow rate blower is configured to move air through said incubator at a rate of at least five cubic feet per minute;
   a plenum formed in said chamber and providing an air circulation path through said chamber, said plenum being partially formed by a plate mounted across said chamber and between the inlet and outlet of said blower; and
   a VOC filter removably attached to the inlet of said blower, said VOC filter being disposed within the gaseous environment of said chamber.

2. The controlled atmosphere incubator of claim 1 further including a HEPA filter coupled to said VOC filter and contained within said chamber.

3. The controlled atmosphere incubator of claim 2 wherein said VOC filter is disposed circumferentially about said HEPA filter.

4. The controlled atmosphere incubator of claim 2 wherein said VOC filter further includes a first molecular sieve element.

5. The controlled atmosphere incubator of claim 4 wherein said first molecular sieve element is selected from the group consisting of carbon, activated carbon, silica, zeolites, and silica zeolites.

6. The controlled atmosphere incubator of claim 5 wherein said VOC filter further includes a second molecular sieve element.

7. The controlled atmosphere incubator of claim 6 wherein said second molecular sieve element is selected from the group consisting of carbon, activated carbon, silica, zeolites, and silica zeolites.

8. The controlled atmosphere incubator of claim 1 wherein said plate is mounted adjacent an upper wall of said chamber to form said plenum between said plate and said upper wall.

9. The controlled atmosphere incubator of claim 8 wherein said inlet extends below said plate and said VOC filter is mounted adjacent to a lower surface of said plate.

10. A controlled atmosphere incubator comprising:
    a cabinet including a chamber having walls enclosing an interior incubating space;
    a plenum formed in said chamber and providing an air flow path through said chamber;

a high flow rate blower mounted in said air flow path of said chamber, said air flow path extending through said interior incubating space, wherein said high flow rate blower is configured to move air along said air flow path through said incubator at a rate of at least five cubic feet per minute;

a HEPA filter removably mounted within said chamber and in said air flow path to filter air traveling to said blower; and a VOC filter removably mounted within the gaseous environment of said chamber and coupled to said HEPA filter, wherein one of said VOC filter and said HEPA filter is disposed circumferentially about the other of said VOC filter and said HEPA filter.

11. The controlled atmosphere incubator of claim 10 wherein said VOC filter is disposed circumferentially about said HEPA filter.

12. The controlled atmosphere incubator of claim 10 wherein said VOC filter further includes a first molecular sieve element.

13. The controlled atmosphere incubator of claim 12 wherein said first molecular sieve element is selected from the group consisting of carbon, activated carbon, silica, zeolites, and silica zeolites.

14. The controlled atmosphere incubator of claim 13 wherein said VOC filter further includes a second molecular sieve element.

15. The controlled atmosphere incubator of claim 14 wherein said second molecular sieve element is selected from the group consisting of carbon, activated carbon, silica, zeolites, and silica zeolites.

* * * * *